United States Patent [19]
Schwarcz et al.

[11] Patent Number: 5,786,508
[45] Date of Patent: *Jul. 28, 1998

[54] SUBSTITUTED KYNURENINES AND PROCESS FOR THEIR PREPARATION

[75] Inventors: Robert Schwarcz, Baltimore, Md.; Mario Varasi, Milan, Italy; Arturo Della Torre, Varese, Italy; Carmela Speciale; Alberto Bianchetti, both of Milan, Italy

[73] Assignees: Pharmacia & Upjohn S.p.A., Milan, Italy; University of Maryland at Baltimore, Baltimore, Md.

[*] Notice: The term of this patent shall not extend beyond the expiration date of Pat. No. 5,519,055

[21] Appl. No.: 411,656

[22] PCT Filed: Jul. 15, 1994

[86] PCT No.: PCT/US94/07804

§ 371 Date: Apr. 6, 1995

§ 102(e) Date: Apr. 6, 1995

[87] PCT Pub. No.: WO95/04714

PCT Pub. Date: Feb. 16, 1995

[51] Int. Cl.$^6$ .................... A61K 31/195; C07C 239/36
[52] U.S. Cl. .................... 562/444; 560/39; 514/564; 514/563; 514/535; 514/538
[58] Field of Search .................... 562/452, 455, 562/444; 560/39; 514/564, 563, 535, 538

[56] References Cited

U.S. PATENT DOCUMENTS 5,495,044   2/1996   Phillips et al. .................... 562/449

FOREIGN PATENT DOCUMENTS

| 0501378 | 9/1992 | European Pat. Off. . |
| WO9218003 | 10/1992 | WIPO . |
| WO9503271 | 2/1995 | WIPO . |
| WO9511878 | 5/1995 | WIPO . |

OTHER PUBLICATIONS

Kawashima, K., et al, An intensely sweet analog of kynurenine: 3–(4–chloroanthraniloyl)–DL–alanine *J. Agric. Food Chem.*, (1980), 28(6), 1338–40. (CA 93:239866) (Abstract).
Tanizawa, K., et al, "The mechanism of kynurenine hydrolysis catalyzed by kynureninase" *J. Biochem.*, (1979), 86(5), 1199–209. (CA 92(5):36767u) (Abstract).
Rivett D., et al, "A synthesis of some model kynurenine peptides." *Aust. J. Chem.*, (1976), 29(9), 2095–100. (CA 85(25):193113a) (Abstract).
Japanese Patent Application No. J8 2018–458 of Tanable SeiyakuKK (Abstract), 1974.
Chemical Abstracts, vol. 93, 1980, 239866u.
J. Med. Chem., 1994, 37, 334–36.
Society for Neuroscience, vol. 19, 1993, Abstract 554.7.
Society for Neuroscience, vol. 18, 1992, Abstract 482.12.
Adv. in Enzym. 1979, 49, 1–40.
Chemical Abstracts, vol. 79, 1973, 28836g.

*Primary Examiner*—Keith D. MacMillan
*Attorney, Agent, or Firm*—Sughrue, Mion, Zinn, Macpeak & Seas, PLLC

[57] ABSTRACT

The present invention relates to the use in the treatment of cognitive disorders associated with the aging processes of the brain and perinatal brain disorders of compounds which act as inhibitors of the enzyme kynurenine aminotransferase (KAT).

The present invention also provides, as novel compounds, a selected class of KAT inhibitors which are the compounds of formula (IA)

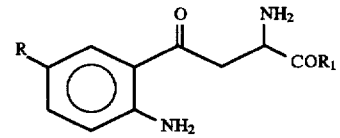

wherein

R is halogen, $C_1$–$C_6$ alkyl, $C_5$–$C_7$ cycloalkyl, phenyl-$C_1$–$C_4$ alkyl, $C_1$–$C_6$ alkoxy, $C_6$–$C_{10}$ aryloxy, phenyl-$C_1$–$C_4$ alkoxy or trifluoromethyl, and $R_1$ is hydroxy, $C_1$–$C_6$ alkoxy, amino, mono-$C_1$–$C_6$ alkylamino, di-$C_1$–$C_6$ alkylamino, hydroxylamino, $C_1$–$C_4$ alkoxyamino or benzyloxyamino, with the provisos that:
(i) when $R_1$ is hydroxy and, at the same time, R is halogen, then this halogen is not fluorine; and
(ii) when $R_1$ is hydroxy and, at the same time, R is $C_1$–$C_6$ alkyl, then this $C_1$–$C_6$ alkyl is not methyl, either as a single isomer or as a mixture of isomers, and the pharmaceutically acceptable salts thereof.

4 Claims, No Drawings

SUBSTITUTED KYNURENINES AND PROCESS FOR THEIR PREPARATION

The present invention relates to a new medical use for certain chemical compounds as well as to novel compounds, to a process for their preparation and to pharmaceutical compositions containing them.

In particular, the invention relates to the use in the treatment of cognitive disorders associated with the aging processes of the brain of compounds which act as inhibitors of the enzyme Kynurenine Aminotransferase (known in the art as KAT).

Compounds which act as KAT inhibitors may be identified using a standard test, for example, measuring their ability to inhibit KAT activity in rat brain homogenate as described, for example, in J. Neurochem., 57, 533–540 (1991) or their inhibitory effect on Kynurenic Acid (KYNA) production by rat brain slices as described, for example, in J. Neurochem., 52, 1629–1636 (1989).

KAT catalyzes the biosynthesis of KYNA from Kynurenine (KYN):

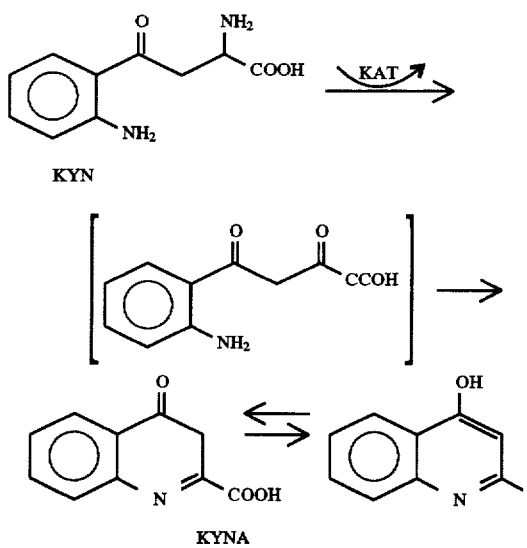

KYN

KYNA and it is singularly responsible for the regulation of extracellular KYNA concentrations in the brain (J. Neurochem., 57, 533–540, 1991).

KYNA is an effective excitatory amino acid (EAA) receptor antagonist with a particularly high affinity to the glycine modulatory site of the N-methyl-D-aspartate (NMDA) receptor complex (J. Neurochem., 52, 1319–1328, 1989).

As a naturally occurring brain metabolite (J. Neurochem., 51, 177–180, 1988 and Brain Res., 454, 164–169, 1988), KYNA probably serves as a negative endogenous modulator of cerebral glutamatergic function (Ann. N.Y. Acad. Sci., vol. 648, p. 140–153, 1992).

EAA receptors and in particular NMDA receptors are known to play a central role in the function of the mammalian brain (J. C. Watkins and G. L. Collingridge—eds.—, The NMDA receptor, Oxford University Press, Oxford, 1989, pp. 242). For example, NMDA receptor activation is essential for cognitive processes, such as, for example, learning and memory (J. C. Watkins and G. L. Collingridge—eds.—, In: The NMDA receptor, Oxford University Press, Oxford, p. 137–151, 1989) and for brain development (Trends Pharmacol. Sci., 11, 290–296, 1990).

It follows that a reduction in NMDA receptor function will have detrimental consequences for brain physiology and, consequently, for the entire organism. For example, the decline in the number of NMDA receptors which occurs in the aged brain (Synapse, 6, 388–343, 1990) is likely associated with age-related disorders of cognitive functions.

In the brain, KYNA concentrations and the activity of KYNA's biosynthetic enzyme KAT show a remarkable increase with age (Brain Res. 558, 1–5, 1992 and Neurosci. Lett., 94, 145–150, 1988). KAT inhibitors, by providing an increase of the glutamatergic tone at the NMDA receptor, could therefore be particularly useful in situations where NMDA receptor function is insufficient and/or KAT activity and KYNA levels are abnormally enhanced. Hence they could be particularly useful in the treatment of the pathological consequences associated with the aging processes in the brain which are, for example, cognitive disorders including, e.g., attentional and memory deficits and vigilance impairments in the elderly.

KAT inhibitors may also be useful in the treatment of perinatal brain disorders which may be related to irregularities in the characteristic region specific pattern of postnatal KAT development (H. Baran and R. Schwarcz: Regional differences in the ontogenic pattern of KAT in the rat brain, Dev. Brain Res., in press).

Accordingly, the first object of the present invention includes the use of KAT inhibitors in the treatment of perinatal brain disorders.

In the present specification, the term "treatment" includes "prophylactic treatment" as well as "the acute alleviation of symptoms".

Particular compounds for use as KAT inhibitors according to the present invention are 5-substituted kynurenine derivatives of the following formula (I)

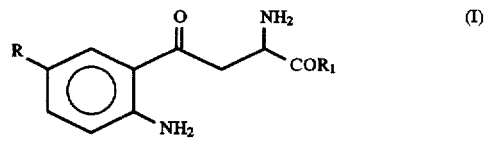

wherein

R is halogen, $C_1$–$C_6$ alkyl, $C_5$–$C_7$ cycloalkyl, phenyl-$C_1$–$C_4$ alkyl, $C_1$–$C_6$ alkoxy, $C_6$–$C_{10}$ aryloxy, phenyl-$C_1$–$C_4$ alkoxy or trifluoromethyl; and $R_1$ is hydroxy, $C_1$–$C_6$ alkoxy, amino, mono-$C_1$–$C_6$ alkylamino, di-$C_1$–$C_6$ alkylamino, hydroxylamino, $C_1$–$C_4$ alkoxyamino or benzyloxyamino.

The invention includes also the use as KAT inhibitors of the pharmaceutically acceptable salts of the compounds of formula (I), as well as the possible isomers covered by the formula (I), both separately and in mixture.

The present invention also describes, as new compounds, some among the compounds of the above formula (I).

These compounds, which form a second object of the present invention, are compounds of formula (IA)

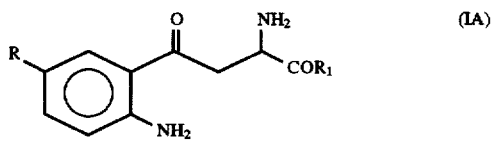

wherein

R is halogen, $C_1$–$C_6$ alkyl, $C_5$–$C_7$ cycloalkyl, phenyl-$C_1$–$C_4$ alkyl, $C_1$–$C_6$ alkoxy, $C_6$–$C_{10}$ aryloxy, phenyl-$C_1$–$C_4$ alkoxy or trifluoromethyl; and $R_1$ is hydroxy, $C_1$–$C_6$ alkoxy, amino, mono-$C_1$–$C_6$ alkylamino, di-$C_1$–$C_6$ alkylamino, hydroxylamino, $C_1$–$C_4$ alkoxyamino or benzyloxyamino;

with the provisos that:
(i) when $R_1$ is hydroxy and, at the same time, R is halogen, then this halogen is not fluorine; and
(ii) when $R_1$ is hydroxy and, at the same time, R is $C_1$–$C_6$ alkyl, then this $C_1$–$C_6$ alkyl is not methyl.

The invention includes in its second object also the pharmaceutically acceptable salts of the compounds of formula (IA), subject to the above provisos, as well as all the possible isomers covered by the formula (IA), both separately and in mixture.

In the present specification, with reference to both the above formulae (I) and (IA), the features of the various substituents are as follows:

The term "halogen" represents Cl, Br, I or F, preferably it is Cl or Br.

The term "$C_1$–$C_6$ alkyl" includes, for example, methyl, ethyl, n-propyl, isopropyl, n-butyl, isobutyl, t-butyl, n-pentyl, isopentyl and n-hexyl, preferably it is methyl, ethyl, n-propyl or isopropyl.

The term "$C_5$–$C_7$ cycloalkyl" represents a 5 to 7 membered monocarbocyclic ring; preferably it is cyclopentyl or cyclohexyl.

The term "$C_6$–$C_{10}$ aryloxy" includes, for example, phenoxy and naphthoxy; preferably it is phenoxy.

The term "phenyl-$C_1$–$C_4$ alkyl" represents a $C_1$–$C_4$ alkyl group bearing a phenyl group such as, for example, benzyl or 1-phenylethyl; preferably it is benzyl.

The term "phenyl-$C_1$–$C_4$ alkoxy" represents a $C_1$–$C_4$ alkoxy group bearing a phenyl group such as, for example, benzyloxy or 1-phenylethoxy; preferably it is benzyloxy.

The term "$C_1$–$C_6$ alkoxy" includes, for example, methoxy, ethoxy, n-propoxy and isopropoxy; preferably it is methoxy or ethoxy.

The term "$C_1$–$C_6$ alkylamino" includes, for example, methylamino, ethylamino, n-propylamino, isopropylamino and n-butylamino; preferably it is methylamino.

The term "$C_1$–$C_4$ alkoxyamino" includes, for example, methoxyamino, ethoxyamino, n-propoxyamino and isopropoxyamino; preferably it is methoxyamino.

The compounds of formula (I) and (IA) possess an asymmetric carbon atom and therefore they can exist in the form of a racemic mixture of optical isomers (enantiomers) or in the form of an individual optical isomer.

Unless otherwise stated, the S configuration of the asymmetric center of the compounds of formula (I) or (IA) corresponds to the L form of the natural Kynurenine; conversely, the R configuration corresponds to the D form of the natural Kynurenine.

The pharmaceutically acceptable salts of the compounds of formula (I) or (IA) include either the salts with pharmaceutically acceptable acids, either inorganic acids such as, for example, hydrochloric, hydrobromic, nitric and sulfuric, or organic acids such as, for example, citric, tartaric, maleic, fumaric, methanesulfonic or ethanesulfonic, or, when the compounds of formula (I) or (IA) contain an acidic, e.g. a carboxy group, the salts with pharmaceutically acceptable bases such as, for example alkali metal, e.g. sodium or potassium; alkaline-earth metal, e.g. calcium or magnesium; zinc or aluminium; or organic bases, such as, e.g., aliphatic amines such as, e.g., methylamine, diethylamine, trimethylamine, ethylamine and heterocyclic amines such as, e.g., piperidine.

A preferred class of compounds under this invention is represented by the compounds of formula (IA) wherein R is halogen, $C_1$–$C_6$ alkyl or $C_5$–$C_7$ cycloalkyl; and
$R_1$ is hydroxy;
with the provisos that:

(i) when R is halogen, then this halogen is not fluorine; and
(ii) when R is $C_1$–$C_6$ alkyl, then this $C_1$–$C_6$ alkyl is not methyl, either as single isomer or as a mixture of isomers, and the pharmaceutically acceptable salts thereof.

Specific examples of preferred compounds of the above formula (IA) are:
2-amino-4-(2-amino-5-chlorophenyl)-4-oxo-butyric acid;
2-amino-4-(2-amino-5-ethylphenyl)-4-oxo-butyric acid;
2-amino-4-(2-amino-5-bromophenyl)-4-oxo-butyric acid;
2-amino-4-(2-amino-5-n-propylphenyl)-4-oxo-butyric acid;
2-amino-4-(2-amino-5-isopropylphenyl)-4-oxo-butyric acid;
2-amino-4-(2-amino-5-cyclohexylphenyl)-4-oxo-butyric acid;
either as a single isomer or as a mixture of isomers, and the pharmaceutically acceptable salts thereof.

The compounds of formula (I) or (IA) of the present invention may be prepared according to a process which comprises:

1) reacting a compound of formula (II)

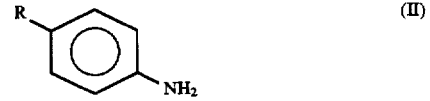

wherein
R is as defined above with reference to formula (I) or (IA) with chloroacetonitrile, so obtaining a compound of formula (III)

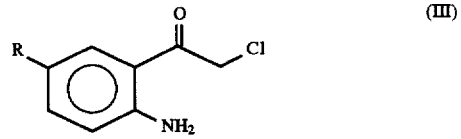

wherein
R is as defined above;

2) reacting a compound of formula (III) with the sodium salt of diethylacetamidomalonate, so obtaining a compound of formula (IV)

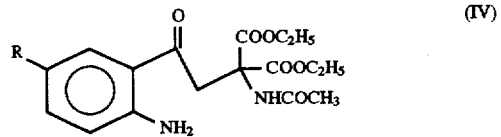

wherein
R is as defined above;

3) treating a compound of formula (IV) with concentrated hydrochloric acid, so obtaining a compound of formula (I) or (IA) wherein R is as defined above and $R_1$ is hydroxy; and, if desired, converting a compound of formula (I) or (IA) into another compound of formula (I) or (IA) with an $R_1$ moiety different from hydroxy; and, if desired, salifying a compound of formula (I) or (IA); and, if desired, separating the isomeric mixture of a compound of formula (I) or (IA) into the single isomers.

Alternatively, the compounds of formula (I) or (IA) can be directly obtained as single isomers by orienting stereospecifically the synthetic process.

The reaction between a compound of formula (II) and chloroacetonitrile may be accomplished, for example, by adding, to a stirred solution of boron trichloride, in methylene chloride a solution of a compound of formula (II) in dry benzene, followed by addition of chloroacetonitrile and aluminium trichloride and refluxing the resulting mixture for about 20 hours.

The reaction between a compound of formula (III) and the sodium salt of acetamidomalonate may be carried out, for example, by adding to a solution of sodium in ethanol diethylacetamidomalonate (dissolved in ethanol), followed by a compound of formula (III), keeping the reaction mixture for 20 hours at room temperature and then heating for 4 hours at 40° C.

The reaction between a compound of formula (IV) and concentrated hydrochloric acid may be carried out, for example, by refluxing for about 7 hours a solution of a compound of formula (IV) in concentrated hydrochloric acid.

Compounds of formula (I) or (IA), wherein $R_1$ is other than hydroxy, can be easily prepared by procedures well known to one of ordinary skill in the art, starting from compounds of formula (I) or (IA) wherein R is as defined above and $R_1$ is hydroxy.

The salification of a compound of formula (I) or (IA) may be carried out according to known methods; typically, by reacting a compound of this invention with the suitable amount of a salt forming reagent.

As already said, the compounds of formula (I) or (IA) have one asymmetric carbon atom and therefore these compounds can exist either as racemic mixture or as individual optical isomers (enantiomers). Therefore, these products may be synthesized either as a mixture of the isomers and then the desired isomer separated by conventional techniques, or synthesis may be carried out by known stereospecific processes.

The separation into the single optical isomers from the corresponding racemic mixture may be carried out, for example, transforming a racemic compound of formula (I) or (IA) into an N-protected compound using a suitable aminoacid protecting group, such as, e.g., acetyl, carbobenzyloxycarbonyl or, tert-butyloxycarbonyl, following methods known in the art. The resulting N-protected derivative of a racemic compound of formula (I) or (IA) can be then recrystallized after salification with a suitable optically active amine, such as, e.g., α-methylbenzylamine, brucine or cinchonine, in the presence of a suitable solvent such as, e.g., ethyl acetate or dioxane, to give an enantiopure diastereoisomeric salt of a compound of formula (I) or (IA) which can be deprotected by known procedures to give the resolved (R) or (S) enantiomer of a compound of formula (I) or (IA).

Alternatively, the compounds of formula (I) or (IA) can be directly obtained as single isomers, by orienting stereospecifically the synthetic process.

For example, reacting a compound of formula (V)

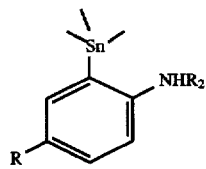

wherein

R is halogen, $C_1$–$C_6$ alkyl, $C_5$–$C_7$ cycloalkyl, phenyl-$C_1$–$C_4$ alkyl, $C_1$–$C_6$ alkoxy, $C_6$–$C_{10}$ aryloxy, phenyl-$C_1$–$C_4$ alkoxy or trifluoromethyl; and $R_2$ is $COR_3$ or $COOR_3$ where $R_3$ is $C_1$–$C_6$ alkyl, with a compound of formula (VIA) or (VIB)

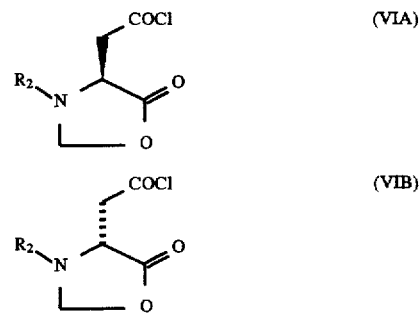

wherein $R_2$ is as defined above in the compound of formula (V), and hydrolysing the resulting compound with a suitable hydrolysing agent such as, e.g., HCl or HBr, the pure enantiomers of a compound of formula (I) or (IA) wherein R is as defined above and $R_1$ is hydroxy are obtained.

A pure enantiomer of a compound of formula (I) or (IA) wherein $R_1$ is hydroxy may be transformed into another compound of formula (I) or (IA) with the substituent $R_1$ different from hydroxy, by standard operations well known by one skilled in the art.

The reaction between a compound of formula (V) and a compound of formula (VIA) or (VIB) may be accomplished, for example, by mixing the reagents in the presence of a suitable palladium complex, such as, e.g., tris (dibenzylideneacetone)dipalladium(O)-chloroform adduct.

A compound of formula (V) can be prepared by methods known in the art (J. Org. Chem. 1979, 44, 1133).

A compound of formula (VIA) or (VIB) can also be prepared by methods known in the art (J. Org Chem. 1988, 53, 6138).

In the compounds of formula (VIA) or (VIB) the term $C_1$–$C_6$ alkyl has the same meanings as in the compounds of formula (I) or (IA).

Alternatively, an enantiomeric pure compound of formula (I) or (IA) can be obtained, for example, by reacting a racemic compound of formula (I) or (IA) or a reactive derivative thereof with a suitable optically pure amine, such as, e.g., (R)-(−)- or (S)-(+)-2-amino-2-phenylethanol, in a suitable solvent, such as, e.g., dimethylformamide (DMF), at a temperature of, e.g., from about 5° to about 25° C., for a time which may vary, e.g., from about 1 hour to about 48 hours. The diastereoisomers thus obtained can be separated chromatographically to give the pure epimers (namely diastereoisomers that differ in configuration at only one asymmetric center) which can be hydrolysed by a suitable hydrolysing agent, such as, e.g., HCl or HBr, to obtain an enantiopure compound of formula (I) or (IA).

The substituted anilines corresponding to the compounds of formula (II) employed as starting materials in the synthesis of the compounds of this invention are commercially available compounds or can be prepared by procedures well known to those of ordinary skill in the art.

The efficacy of the compounds of formula (I) or (IA) in inhibiting the enzyme Kynurenine Aminotransferase (KAT) has been demonstrated in the following tests A), B) and C).

A) Determination of KAT activity inhibition in rat brain homogenate

KAT was measured as described in detail by Okuno et al. (Measurement of rat brain kynurenine amino-transferase at physiological kynurenine concentrations. J. Neurochem., 57, 533–540, 1991).

Briefly, animals were killed by decapitation and the brain tissue was homogenized (1:5 v/w in 5 mM Tris-acetate buffer, pH 8.0, containing 10 mM 2-mercaptoethanol and 50

μM pyridoxal 5'-phosphate) and incubated for 2 h at 37° C. in the presence of 2 μM [$^3$H]KYN (30 nCi), 1 mM 2-oxoglutarate and 70 μM pyridoxal 5'-phosphate in 150 mM Tris-acetate buffer, pH 8.0. The reaction was terminated by the addition of trichloroacetic acid.

Newly synthesized [$^3$H]KYNA was separated from [$^3$H] KYN on a Dowex 50W cation-exchange column and quantitated by liquid scintillation spectrometry. Blanks were obtained by using tissue which had been heat-deactivated for 10 minutes in a boiling water bath.

When tested under these conditions, the compounds of the present invention were able to inhibit KAT activity.

The results obtained by a representative number of compounds of formula. (I) or (IA) are reported in the in the following Table 1.

included in the incubation mixture as needed. Following incubation, the culture wells were immediately placed on ice, and the slices were rapidly separated from the incubation medium. For KYNA determination, 1 ml samples of the incubation medium were immersed in a boiling water bath for 10 min, and the precipitated proteins were removed by centrifugation (8,730×g, 10 min). The supernatants were diluted (1:1, v/v) with 0.2M HCl and applied to Dowex 50W (hydrogen form, Sigma) cation-exchange columns (0.5×2 cm). Subsequently, the columns were washed with 1 ml of 0.1M HCl and 1 ml of water, and the fraction containing KYNA was eluted with 2 ml of water. The eluates were applied to a 3-μm $C_{18}$ HPLC column (100×3.2 internal diameter, Bioanalytical Systems, West Lafayette, Ind., U.S.A.), and KYNA was isocratically eluted with a mobile

TABLE 1

Compound

| | | | KYNA production % of inhibition | |
|---|---|---|---|---|
| | R | Configuration | 1000 μM | 100 μM |
| FCE 27813 | Cl | DL | 81 | 45 |
| FCE 28442 | Cl | D | 31 | nc |
| FCE 28443 | Cl | L | 89 | 61 |
| FCE 28264 | Br | DL | 83 | 52 |
| FCE 27949 | F | DL | 74 | 30 |
| FCE 27946 | Me | DL | 51 | 13 |
| FCE 28026 | Et | DL | 78 | 30 |
| FCE 28244 | n-Pr | DL | 72 | 50 |
| FCE 28441 | i-Pr | DL | 72 | 45 |
| FCE 28263 | cyclohexyl | DL | 77 | 47 | nc = not calculated

B) Determination of inhibition of KYNA production by rat tissue slices

Routinely, slices (base 1×1 mm; weight 1.5 mg/slice) from the cerebral cortex were separated on ice and transferred to culture wells (10 slices/well) containing 1 ml of oxygenated Krebs-Ringer buffer (NaCl, 118.5 mM; KCl, 4.75 mM; CaCl$_2$, 1.77 mM; MgSO$_4$, 1.18 mM; NaH$_2$PO$_4$, 12.9 mM; NaH$_2$PO$_4$, 3 mM; glucose, 5 mM; pH 7.4). Subsequently, the tissue was preincubated for 10 min at 37° C. and incubated further for 2 h at 37° C., in the presence of 50 μM L-KYN in an oxygenated chamber, on a shaking water bath. Compounds of the present invention were phase containing 50 mM ammonium acetate and 5% methanol at a flow rate of 0.5 ml/min. Under these conditions, the retention time of KYNA was ≈7 min.

Data were recorded and calculated with a Hewlett-Packard 3390A integrator connected to a model 160 UV absorbance detector (Beckman Instruments, Berkeley, Calif., U.S.A.) set at 340 nm.

In this assay a representative number of compounds of formula (I) or (IA) were tested and the obtained results are reported in the following Table 2.

TABLE 2

Compound

| | | | KYNA production % of inhibition | |
|---|---|---|---|---|
| | R | Configuration | 1000 μM | 100 μM |
| FCE 27813 | Cl | DL | 84 | 63 |
| FCE 28442 | Cl | D | 45 | nc |
| FCE 28443 | Cl | L | 91 | 67 |
| FCE 28264 | Br | DL | 72 | 58 |
| FCE 27949 | F | DL | 70 | 48 |
| FCE 27946 | Me | DL | 64 | 50* |
| FCE 28026 | Et | DL | 49 | 8 |
| FCE 28244 | n-Pr | DL | 70 | 27 |
| FCE 28441 | i-Pr | DL | 54 | 5 |
| FCE 28263 | cyclohexyl | DL | 45 | 28 |

*at 300 μM nc = not calculated

The abbreviations used in the above Table 1 and 2: Me, Et, n-Pr, i-Pr stand respectively for methyl, ethyl, n-propyl and isopropyl.

C) Kinetic analysis of KAT inhibitors using a partially Purified enzyme Preparation (Brain Research, 534, 37–44 (1990)

The reaction mixture contained [$^3$H]KYN (30 nCi), diluted with unlabelled KYN to yield a final concentration of 2 µM, 1 mM pyruvate, 70 µM pyridoxal 5'-phosphate, 150 mM Tris-acetate buffer, pH 8.0, and a preparation of partially purified enzyme in a total volume of 0.1 ml. Test compounds were included in the incubation mixture as needed. The reaction was started by the addition of pyruvate. After incubation for 2 h at 37° C., the reaction was terminated by the addition of 14 µl of 50% (w/w) trichloroacetic acid. Subsequently, 1 ml of 0.1M HCl was added and denaturated protein was removed by a 4-min centrifugation in a Beckman 52B microfuge. 1 ml of the resulting supernatant was applied to a Dowex 50W column (0.5×1.0 cm; H$^+$ form) and washed with 1 ml of 0.1M HCl, followed by 1 ml of distilled water. [$^3$H]KYNA was eluted with 2 ml of distilled water and quantitated by liquid scintillation spectrometry. Enzyme measurements were performed in triplicate samples. Blanks were obtained by using an enzyme preparation which had been heat-deactivated for 10 min in a boiling water bath.

Kinetic experiments were performed using the standard KAT assay described above by varying the concentration of KYN between 2 µM and 2 mM in the absence or presence of set concentrations of test compounds. Double reciprocal plots were constructed and lines of best fit were determined by linear regression analysis.

Kinetic constants:

| L-kynurenine $K_m$ | D,L-5-Cl,kynurenine $K_i$ |
|---|---|
| 369 µM | 88 µM |

The present invention includes in its scope also the pharmaceutical compositions containing as an active substance therapeutically effective amount of a compound of formula (I) or (IA) or a pharmaceutically acceptable salt thereof as well as any possible isomer, or mixture of isomers, covered by the formula (I) or (IA) in association with one or more pharmaceutically acceptable carriers, diluent or excipient thereof. Mammalian, such as human, are treatable with the inventive pharmaceutical composition.

The compounds of the invention can be administered by the usual routes, for example, parenterally, e.g. by intravenous injection or infusion, intramuscularly, subcutaneously, topically, orally or in a form suitable for administration by inhalation or insufflation.

The dosage depends on the age, weight and conditions of the patient, the potency of the compounds and on the administration route. For example, a suitable dosage for administration to adult humans may range from about 0.1 to about 100 mg per dose of the active substance and may be administered for example 1–4 times a day. The pharmaceutical compositions of the invention are usually prepared following conventional methods and are administered in a pharmaceutically acceptable form.

For instance, solutions for intravenous injection of infusion may contain as carrier, for example, sterile water or, preferably, they may be in the form of sterile aqueous isotonic saline solutions.

Suspensions, solutions or emulsions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

Formulation for injection may contain formulatory agents such as suspending, stabilising, and/or dispersing agents.

Alternatively, the active ingredient may be formulated in powder form for constitution with a suitable vehicle, e.g. sterile pyrogen-free water, before use. In the formulations for topical application, e.g. creams, lotions or pastes, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

The tablets may be coated by methods well known in the art.

The liquid oral forms, e.g. suspensions, syrups or solutions may be prepared by conventional means, for example, with pharmaceutically acceptable additives, preservatives, sweetening agents and/or flavouring agents.

The compositions of the invention may be formulated so as to provide quick, sustained or delayed release of the active substance after administration to the patient by employing procedures well known in the art.

The following examples illustrate but do not limit the invention.

EXAMPLE 1

5-chloro-2-amino-α-chloroacetophenone

To a stirred solution of boron trichloride in methylene chloride (100 ml 1M, 0.1 mol), a solution of 4-chloro-aniline (12.12 g, 0.095 mol) in dry benzene (120 ml) was added dropwise under nitrogen at a temperature ranging from 5° C. to 10° C.

To the resulting mixture, chloroacetonitrile (7.27 ml, 0.115 mol) and aluminium trichloride (13.33 g, 0.1 mol) were added successively. The mixture was refluxed for 20 hours.

After cooling, ice-cold 2N hydrochloric acid (≈100 ml) was added and a yellow precipitate was formed.

The mixture was warmed at 80° C. under stirring, until the precipitate had dissolved (≈45').

The cooled solution was adjusted to pH 2 by addition of 2N NaOH and extracted with dichloromethane (three times).

The organic layer was washed with water, dried (Na$_2$SO$_4$), and concentrated.

The residue was ground with hexane (120 ml) to obtain 9.27 g of the desired product as light brown solid, m.p. 133°–136° C.

By proceeding analogously, the following compounds can be prepared:

5-methyl-2-amino-α-chloroacetophenone, m.p. 127°–129° C.;

5-fluoro-2-amino-α-chloroacetophenone, m.p. 121°–123° C.;

5-ethyl-2-amino-α-chloroacetophenone, m.p. 118°–120° C.;

5-cyclohexyl-2-amino-α-chloroacetophenone, m.p. 88°–91° C.;

5-bromo-2-amino-α-chloroacetophenone, m.p. 127°–130° C.;

5-n-propyl-2-amino-α-chloroacetophenone, m.p. 119°–122° C.; and 5-isopropyl-2-amino-α-cholroacetophenone, m.p. 66°–70° C.

EXAMPLE 2

Ethyl acetamido-(2-amino-5-chlorophenacyl)-malonate

Sodium (1.04 g, 0.0453 mol) was dissolved in ethanol (80 ml) and diethyl acetamidomalonate (9.84 g, 0.0453 mol) in 120 ml of ethanol was added. The solution was warmed at 45° C. for 1 h.

After cooling at room temperature, a solution of 5-chloro-2-amino-α-chloroacetophenone (9.25 g, 0.0453 mol) in 150 ml of ethanol was added dropwise, while stirring and under nitrogen.

The reaction was stirred for 20 h at room temperature, then the mixture was heated at 40° C. for 4 h. The reaction mixture was evaporated to dryness and the residue was taken up with 300 ml of water and 1N NaOH (20 ml) and extracted with diethyl ether.

The organic phase was washed with water, dried and then evaporated to dryness to give a solid which was recrystallized from 210 ml of isopropyl alcohol to obtain 6.02 g of the desired product as a cream solid, m.p. 156°–158° C.

By proceeding analogously, the following compounds can be prepared:

diethyl acetamido-(2-amino-5-methylphenacyl)-malonate, m.p. 179°–181° C.;

diethyl acetamido-(2-amino-5-fluorophenacyl)-malonate, m.p. 143°–145° C.;

diethyl acetamido-(2-amino-5-ethylphenacyl)-malonate, m.p. 121°–123° C.;

diethyl acetamido-(2-amino-5-cyclohexylphenacyl)-malonate, m.p. 89°–93° C.; diethyl acetamido-(2-amino-5-bromophenacyl)-malonate, m.p. 151°–154° C.;

diethyl acetamido-(2-amino-5-n-propylphenacyl)-malonate, m.p. 115°–117° C.; and diethyl acetamido-(2-amino-5-isopropylphenacyl)-malonate, m.p. 110°–115° C.

EXAMPLE 3

2-amino-4-(2-amino-5-chlorophenyl)-4-oxo-butyric acid (D,L-5-chloro-kynurenine)

A solution of diethyl acetamido-(2-amino-5-chlorophenacyl)-malonate (5.3 g, 0.01377 mol) in concentrated hydrochloric acid (60 ml) was refluxed for 7 h under stirring.

The reaction was evaporated to dryness under vacuum and the residue was taken up with water and washed with methylene chloride.

The aqueous layer was concentrated, the residue dissolved in water (100 ml) and the resulting solution was adjusted to pH 6.5 by addition of 2N NaOH to yield the desired product as a yellow precipitate.

The solid was filtered and washed with water to obtain 3.10 g of the desired product, m.p. 236°–238° C. (dec.).

By proceeding analogously, the following compounds can be prepared:

2-amino-4-(2-amino-5-methylphenyl)-4-oxo-butyric acid, m.p. 230°–250° C. (dec.);

2-amino-4-(2-amino-5-fluorophenyl)-4-oxo-butyric acid, m.p. 200°–225° C. (dec.);

2-amino-4-(2-amino-5-ethylphenyl)-4-oxo-butyric acid, m.p. 210° C. (dec.);

2-amino-4-(2-amino-5-cyclohexylphenyl)-4-oxo-butyric acid, m.p. 230°–250° C. (dec.);

2-amino-4-(2-amino-5-bromophenyl)-4-oxo-butyric acid, m.p. 233° C. (dec.);

2-amino-4-(2-amino-5-n-propylphenyl)-4-oxo-butyric acid, m.p. 233°–234° C.; and 2-amino-4-(2-amino-5-isopropylphenyl)-4-oxo-butyric acid, m.p. 235° C. (dec.).

EXAMPLE 4

(S)(−)-2-amino-4-(2-amino-5-chlorophenyl)-4-oxo-butyric acid (L-5-chloro-kynurenine) and (R)-(+)-2-amino-4-(2-amino-5-chlorophenyl)-4-oxo-butyric acid (D-5-chloro-kynurenine) by diastereomeric salt resolution To a stirred solution of 2-amino-4-(2-amino-5-chlorophenyl)-4-oxo-butyric acid (5.23 g, 21.55 mmol), $NaHCO_3$ (3.98 g, 47.4 mmol) and $Na_2CO_3.10H_2O$ (6.16 g, 21.55 mmol) in 300 ml of water, acetic anhydride (2.236 ml, 23.7 mmol) was added dropwise at room temperature.

The solution was stirred for 1 h, acidified to pH 5 with 2N HCl and extracted with ethyl acetate (four times), washed with water, dried and evaporated to give a light yellow solid.

The crude product was ground with hexane to obtain 2-acetamido-4-(2-amino-5-chlorophenyl)-4-oxo-butyric acid (4.20 g; 68.4%; m.p. 187°–190° C.).

To a stirred solution of 2-acetamido-4-(2-amino-5-chlorophenyl)-4-oxo-butyric acid (4.20 g, 14.75 mmol) in 500 ml of 95% ethanol, R-(+)-α-methylbenzylamine (1.88 ml, 14.75 mmol) was added dropwise. After 20 min the solvent was evaporated: the residue was ground with diethyl ether to obtain a solid (5.10 g ; m.p. 130°–150° C.; $[\alpha]^{20}_D$= +2.5° (1%, $CH_3OH$)).

Four further recrystallizations from ethyl acetate yielded 1.12 g (enantiomeric yield 37%) of the (−)-α-methylbenzylamine salt of 2-acetamido-4-(2-amino-5-chlorophenyl)-4-oxobutyric acid (m.p. 154.5°–156° C.; $[\alpha]_D^{20}$=−60.8° (1%, $CH_3OH$).

To a vigourously stirred solution of (−)-α-methylbenzylamine salt (1.12 g, 2.76 mmol) in ethyl acetate (110 ml), water (20 ml) and then 1N HCl (2.9 ml, 2.9 mmol) were added. After 30 min the organic phase was separated and the aqueous phase was extracted with ethyl acetate. The combined organic phases were washed with water, dried and evaporated to give (−)-2-α-acetamido-4-(2-amino-5-chlorophenyl)-4-oxo-butyric acid (0.76 g; 97%) as a light brown solid (m.p. 182°–183.5° C.(dec.); $[\alpha]_D^{20}$=−88.7° (1%, $CH_3OH$).

A solution of (−)-2-acetamido-4-(2-amino-5-chlorophenyl)-4-oxo-butyric acid (0.76 g, 2.67 mmol) in 2N HCl (90 ml) was heated at reflux temperature for 3 h. The aqueous solution was evaporated to dryness, the residue was dissolved in water, washed with $CH_2Cl_2$ and evaporated again. The residue was dissolved in water (30 ml) and adjusted to pH 6.5 with 1N NaOH: a light yellow solid separated. The solid was filtered and washed with cold water to obtain (R)-(+)-2-amino-4-(2-amino-5-chlorophenyl)-4-oxo-butyric acid (0.40 g; 59.7%; m.p. 210°–211° C. (dec.); $[\alpha]^{20}{}_D$=+11.5 (1%, CH$_3$COOH); ee=96%).

The mother liquors obtained during the preparation of the (−)-α-methylbenzylamine salt were mixed and evaporated to give 4.9 g (12 mmol) of a solid. This mixture of (−) and (+) salt was vigourously stirred with ethyl acetate (400 ml), water 80 ml) and 1N HCl (12.6 ml, 12.6 mmol). After 30 min. the organic phase was separated and the aqueous phase was extracted with ethyl acetate. The combined organic phases were washed with water, dried and evaporated to give 2-acetamido-4-(2-amino-5-chlorophenyl)-4-oxo-butyric acid (light brown solid) enriched in the (+)-enantiomer (3.41 g; 100%; m.p. 172°–178° C.).

To a stirred solution of 2-acetamido-4-(2-amino-5-chlorophenyl)-4-oxo-butyric acid (3.41 g, 11.97 mmol) in 400 ml of 95% ethanol, S-(−)-α-methylbenzylamine (1.52 ml, 11.97 mmol), was added dropwise. After 20 min the solvent was evaporated. Three recrystallizations from ethyl acetate afforded 1.49 g (61.3%) of the (+)-α-methylbenzylamine salt of 2-acetamido-4-(2-amino-5-chlorophenyl)-4-oxo-butyric acid, (m.p. 154.5°–155.5° C.; $[\alpha]^{20}{}_D$=+60.9 (1%, CH$_3$OH))

1.49 g of the salt above were processed as previously described for the (−)-enantiomer and afforded 1.03 g (98.5%) of (+)-2-acetamido-4-(2-amino-5-chlorophenyl)-4-oxo-butyric acid (m.p. 179°–180° C. (dec.); $[\alpha]^{20}{}_D$=+89.0 (1% CH$_3$OH).

Starting from 1.03 g. of (+)-2-acetamido-4-(2-amino-5-chlorophenyl)-4-oxo-butyric acid as described above for the preparation of (R)-enantiomer, 0.65 g (71.4%) of (S)-(−)-2-amino-4-(2-amino-5-chlorophenyl)-4-oxo-butyric acid were obtained (m.p. 208°–209° C. (dec.); $[\alpha]^{20}{}_D$=−12.6° (1%, CH$_3$COOH); ee=96%).

EXAMPLE 5

(S)-(−)-2-amino-4-(2-amino-5-chlorophenyl)-4-oxo-butyric acid (L-5-chlorokynurenine) and (R)-(+)-2-amino-4-(2-amino-5-chlorophenyl)-4-oxo-butyric acid (D-5-chlorokynurenine) by enantiospecific synthesis A solution of 4-chloro N-pivaloylaniline* (2.11 g, 10 mmol) in 30 ml of dry THF was cooled in an ice bath under an atmosphere of nitrogen. Then an hexane solution of 1.6M of n-BuLi (15.625 ml, 25 mmol) was added dropwise. After stirring at 0° C. for 2.5 h, trimethyltin chloride (2.19 g, 11 mmol) dissolved in dry THF (8 ml) was added within 20 min at 0° C. The reaction was then stirred for 2 h at 0° C. and for 16 h at room temperature, quenched with water and extracted with ethyl acetate. The organic layer was washed with brine, dried and concentrated to dryness. The residue was purified by flash chromatography on silica gel (diisopropylether: petroleum ether 40°/70°=10:23) to yield 4-chloro-2-trimethylstannyl-N-pivaloylaniline as a white solid 3.1 g; 82.9%; m.p. 169°–172° C.).

* JOC 44, 1133 (1979)

4-chloro-2-trimethylstannyl-N-pivaloylaniline (1.6 g., 4.2 mmol) and (S)-3-benzyloxycarbonyl-5-oxo-4-oxazo-lidineacetyl chloride* (1.25 g., 4.2 mmol) were dissolved in anhydrous toluene (50 ml). To this solution Pd$_2$(dba)$_3$CHCl$_3$ (40.5 mg) was added and the mixture was heated at 70° C. for 8 h. The mixture was cooled, and the catalyst was removed by filtration over celite.

The filtrate was concentrated and then diluted with ethyl acetate; the resulting solution was washed consecutively with saturated bicarbonate, water, and saturated NaCl, then dried and evaporated. The residue was purified by flash chromatography on silica gel (ethyl acetate: hexane=8:30) to obtain (S)-(+)-N-pivaloyl-2-[1-oxo-2-[-3-(benzyloxycarbonyl)-5-oxo-oxazolidin-4-yl]-ethyl]-4-chloro-aniline as colorless crystals 1.06 g (53.5%); m.p. 113°–116° C. ; $|\alpha|^{20}{}_D$=−114.5 (1%; ethyl acetate)

* JOC 53, 6138 (1988).

A stirred mixture of (S)-(+)-N-pivaloyl-2-[1-oxo-2-[3-(benzyloxycarbonyl)-5-oxo-oxazolidin-4-yl]ethyl]-4-chloro aniline (1.06 g, 2.24 mmol), 37% HCl (20 ml), H$_2$O (20 ml) and CH$_3$COOH (28 ml), was heated at 70° C. for 5.5 h. The solution was evaporated to dryness. The residue was dissolved in water (30 ml), washed with CH$_2$Cl$_2$ and evaporated again. The crude product was purified by flash chromatography on silica gel (chloroform: methanol:30% NH$_4$OH=140:60:6) to yield (S)-(−)-2-amino-4-(2-amino-5-chlorophenyl)-4-oxo butyric acid as yellow crystal (0.29 g; 51.5%; m.p. 206°–208° C.; $[\alpha]^{20}{}_D$=−12.0° (1%; CH$_3$OOH); ee 96%.

By proceeding analogously, the following compound can be prepared:

(R)-(+)-2-amino-4-(2-amino-5-chlorophenyl)-4-oxo-butyric acid (D-5-chlorokynurenine); $[\alpha]_D{}^{20}$=+11.5° (1%, CH$_3$COOH).

EXAMPLE 6

(S)-2-amino-4-(2-amino-5-chlorophenyl)-4-oxo-butyric acid (L-5-chlorokynurenine) and (R)-(+)-2-amino-4-(2-amino-5-chlorophenyl)-4-oxo-butyric acid (D-5-chlorokynurenine) by formation and chromatographic separation of diastereoisomers To a stirred solution of 2-acetamido-4-(2-amino-5-chlorophenyl)-4-oxo-butyric acid (0.569 g; 2 mmol) in dry DMF (8 ml), 1,1'-carbonyldiimidazole (0.34 g; 2.1 mmol) was added portionwise at 5°–8° C. under nitrogen. After stirring at 5° C. for 1.5 h, (R)-(−)-2-amino-2-phenylethanol (0.33 g; 2.4 mmol) in dry DMF (6 ml) was added dropwise at 3°–5° C. The reaction was then stirred for 2 h in an ice bath and 16 h at room temperature, quenched with water and extracted with ethyl acetate. The organic layer was washed with water, dried with an. sodium sulfate and concentrated to dryness. The residue was purified by flash-chromatography on silica gel (ethyl acetate:methanol=98:2) to yield 2-acetylamino-4-(2-amino-5-chlorophenyl)-N-(2-hydroxy-1-phenyl-ethyl)-4-oxobutyramide as a yellow solid (0.18 g; 22%; m.p. 212°–215° C.) (pure diastereoisomer with Rf<).

A solution of 2-acetylamino-4-(2-amino-5-chlorophenyl)-N-(2-hydroxy-1-phenyl-ethyl)-4-oxo-butyramide (pure diastereoisomer with Rf<) (0.155g; 0.383 mmol) in 2N HCl (15 ml) was heated at reflux for 6 h. The solution was evaporated to dryness, the residue dissolved in water, washed with CH$_2$Cl$_2$ and evaporated again. The crude product was purified by flash-chromatography on silica gel (chloroform:methanol:30%ammonia solution=140:60:6) to yield (S)-(−)-2-amino-4-(2-amino-5-chlorophenyl)-4-oxo-butyric acid as a yellow solid (0.048 g; 50%; m.p. 205°–208° C.; $[\alpha]_D{}^{20}$=−12.0° (1%, CH$_3$COOH).

By proceeding analogously, the following compound can be prepared:

(R)-(+)-2-amino-4-(2-amino-5-chlorophenyl)-4-oxo-butyric acid (D-5-chlorokynurenine); $[\alpha]_D{}^{20}$=+11.5° (1%, CH$_3$COOH).

EXAMPLE 7

Tablets for Oral Administration

Tablets may be prepared by known methods such as direct compression or wet granulation.

For example, tablets each weighing 0.250 g and containing 50 mg of the active substance, can be manufactured as follows:

Composition (for 10.000 tablets)

| | |
|---|---|
| 2-amino-4-(2-amino-5-chlorophenyl)-4-oxo-butyric acid | 500 g |
| Lactose | 1400 g |
| Corn starch | 500 g |
| Talc powder | 80 g |
| Magnesium stearate | 20 g |

The 2-amino-4-(2-amino-5-chlorophenyl)-4-oxo-butyric acid, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

Tablets of other strengths may be prepared by modifying the ratio of the active substance to excipients.

EXAMPLE 8

Capsules for Oral Administration

Capsules, each dosed at 0.200 g and containing 20 mg of the active substance can be prepared as follows:

Composition for 500 capsules:

| | |
|---|---|
| 2-amino-4-(2-amino-5-chlorophenyl)-4-oxo-butyric acid | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

EXAMPLE 9

Intramuscular Injection 25 mg/ml

An injectable pharmaceutical composition can be manufactured by dissolving 25 g of 2-amino-4-(2-amino-5-chlorophenyl)-4-oxo-butyric acid sodium salt in water for injection (1000 ml) and sealing ampoules of 1–5 ml.

We claim:

1. A compound selected from the group consisting of:
2-amino-4-(2-amino-5-bromophenyl)-4-oxo-butyric acid;
2-amino-4-(2-amino-5-n-propylphenyl)-4-oxo-butyric acid;
2-amino-4-(2-amino-5-isopropylphenyl)-4-oxo-butyric acid;
2-amino-4-(2-amino-5-cyclohexylphenyl)-4-oxo-butyric acid;
either as a levorotatory isomer or as a mixture of isomers, and the pharmaceutically acceptable salts thereof.

2. A pharmaceutical composition comprising, as an active substance, a therapeutically effective amount of a compound as claimed in claim 1 and a pharmaceutically acceptable carrier, diluent or excipient thereof.

3. A method of treating age-related cognitive disorders and perinatal brain disorders comprising administering a therapeutically effective amount of a pharmaceutical composition as claimed in claim 2 to a patient in need thereof.

4. A method of treating age-related cognitive disorders and perinatal brain disorders comprising administering a therapeutically effective amount of a compound as claimed in claim 1 to a patient in need thereof.

* * * * *